United States Patent [19]

Kuhn et al.

[11] 4,031,213

[45] June 21, 1977

[54] PHARMACEUTICAL COMPOSITION AND METHOD FOR THE TREATMENT OF HYDROPIC CONDITIONS

[75] Inventors: Rolf Kuhn, Mannheim-Waldhof; Klaus Hardebeck, Ludwigshafen (Rhine); Helmut Heinemann, Heidelberg, all of Germany

[73] Assignee: Boehringer Mannheim G.m.b.H., Mannheim-Waldhof, Germany

[22] Filed: Apr. 16, 1975

[21] Appl. No.: 568,640

[30] Foreign Application Priority Data

May 15, 1974 Germany .......................... 2423606

[52] U.S. Cl. .................................. 424/229; 424/21
[51] Int. Cl.$^2$ ......................................... A61L 13/00
[58] Field of Search ..................................... 424/229

[56] References Cited

UNITED STATES PATENTS 3,665,002  5/1972  Popelak et al. ..................... 424/229

FOREIGN PATENTS OR APPLICATIONS 1,121,610  1/1962  Germany ........................... 424/229

*Primary Examiner*—Dale R. Ore
*Attorney, Agent, or Firm*—Burgess, Dinklage & Sprung

[57] ABSTRACT

Pharmaceutical compositions comprising
 a. at least one member of 5-(4-chloro-5-sulfamoyl-2-thenylaminophenyl)-tetrazole and the pharmacologically compatible salts thereof,
 b. 3-(3-oxo-7α-acetylthio-17β-hydroxy-4-androsten-17α-yl)-propionic acid-γ-lactone, and
 c. a pharmaceutical diluent or carrier possess outstanding activity for treating hydropic conditions and prevent undesirable increased excretion of potassium without at the same time impairing the desired excretion of water and sodium.

12 Claims, No Drawings

PHARMACEUTICAL COMPOSITION AND METHOD FOR THE TREATMENT OF HYDROPIC CONDITIONS

The present invention relates to pharmaceutical compositions, more specifically, to compositions for the treatment of various hydropic conditions.

When using 5-(4-chloro-5-sulfamoyl-2-thenylaminophenyl)-tetrazole for the treatment of various hydropic conditions, for example cirrhosis of the liver, cardiac insufficiency, cor pulmonale, respiratory insufficiency, water retention in the case of chronic kidney diseases and hydropic conditions of patients with neoplasms, it is possible to bring about a rapid and effective excretion of the pathologically accumulated water, together with excess mineral salts.

However, when using this active material, an increased excretion of potassium is frequently observed, which can result in a reduction of the potassium content in the body cells and in the blood. This results in disturbances of the actions of the cardiac and skeletal muscles, as well as in metabolic changes, especially in the metabolism of uric acid and carbohydrates.

The composition of the present invention substantially prevents this increased excretion of potassium, without, at the same time, impairing the excretion of water and sodium.

We have now, surprisingly, found that the simultaneous administration of 3-(3-oxo-7α-acetylthio-17β-hydroxy-4-androsten-17α-yl)-propionic acid-γ-lactone, which itself has a diuretic action, can normalize the increased excretion of potassium brought about by 5-(4-chloro-5-sulfamoyl-2-thenylaminophenyl)-tetrazole.

This finding is very surprising since the combined action of the two active materials 5-(4-chloro-5-sulfamoyl-2-thenylaminophenyl)-tetrazole and 3-(3-oxo-7α-acetylthio-17β-hydroxy-4-androsten-17α-yl)-propionic acid-α-lactone substantially increases the excretion of water and sodium but, at the same time, normalizes the excretion of potassium. Thus, by combination of these two diuretics, the necessary excretion of water and sodium can be further increased and, at the same time, the potassium content of the skeletal and cardiac muscle and of the blood can be kept at the desired level.

Thus, the present invention provides a pharmaceutical composition comprising 5-(4-chloro-5-sulfamoyl-2-thenylaminophenyl)-tetrazole and 3-(3-oxo-7α-acetylthio-17β-hydroxy-4-androsten-17α-yl)-propionic acid-γ-lactone, together with a pharmaceutical diluent or carrier.

Similar results are obtained when using the salts of 5-(4-chloro-5-sulfamoyl-2-thenylaminophenyl)-tetrazole and 3-(3-oxo-7α-acetylthio-17β-hydroxy-4-androsten-b 17α-yl)-propionic acid-γ-lactone.

5-(4-Chloro-5-sulfamoyl-2-thenylaminophenyl)-tetrazole, and the pharmacologically compatible salts thereof, are described in U.S. Pat. No. 3,665,002.

3-(3-Oxo-7α-acetylthio-17β-hydroxy-4-androsten-17α-yl)-propionic acid-γ-lactone is described in German Patent Specification No. 1,121,610.

The new pharmaceutical composition according to the present invention is suitable for the treatment of severe hydropic conditions, especially of a chronic nature, such as occur, for examples, in cases of cirrhosis of the liver, cardiac insufficiency, cor pulmonale, respiratory insufficiency, chronic kidney diseases and neoplasms. The new pharmaceutical composition according to the present invention is particularly suitable when, due to the causes of the disease, prolonged therapy is unavoidable.

The above-mentioned active materials are preferably present in the new pharmaceutical compositions in such amounts that for 50 parts by weight of 3-(3-oxo-7α-acetylthio-17β-hydroxy-4-androsten-17α-yl)-propionic acid-γ-lactone there are present 10 to 100 parts and more preferably 15 to 30 parts by weight of 5-(4-chloro-5-sulfamoyl-2-thenylamino-phenyl)-tetrazole.

The daily dosage is preferably about 40 to 400 mg. and especially 65 to 300 mg. of the active material combination. The daily dose can be taken in the morning or can be divided into 3 individual doses spread out over the course of the day.

The composition according to the present invention can be administered orally or parenterally and can be in any form conventionally employed for oral or parenteral administration, for example, tablets, capsules, dragees, syrup solutions, suspensions, drops, suppositories, and the like. For this purpose, the active materials are mixed with solid or liquid carrier materials and subsequently brought into the desired form. Examples of solid carrier materials include lactose, mannitol, starch, talc, methyl cellulose, magnesium stearate and gelatine to which, if desired, coloring and/or flavoring materials can be added. Liquid carrier materials for injection solutions must be sterile and pyrogen-free. They are preferably placed into ampoules.

The new composition according to the present invention is preferably in the form of a dragee or capsule.

The following Examples are given for the purpose of illustrating the present invention. For the sake of brevity, in the following Examples, 3-(3-oxo-7α-acetylthio-17β-hydroxy-4-androsten-17α-yl)-propionic acid-γ-lactone (USP) is referred to as Compound A and 5-(4-chloro-5-sulfamoyl-2-thenylaminophenyl)-tetrazole as Compound B:

EXAMPLE 1.

| | |
|---|---|
| Compound A | 1000.0 g. |
| lactose (DAB) | 2880.0 g. |
| sodium lauryl sulfate (USP) | 120.0 g. | were mixed together and micronized. The mixture was subsequently mixed with

| | |
|---|---|
| Compound B | 300.0 g. |
| lactose (DAB) | 1696.0 g. |
| sodium carboxymethylamylopectin | 200.0 g. |
| highly dispersed silicic acid | 4.0 g. | and granulated in known manner with water, whereafter the granules obtained were dried and sieved. The granulate thus obtained was mixed with

| | |
|---|---|
| corn starch | 160.0 g. |
| magnesium stearate | 40.0 g. |

The mixture thus obtained containing the active materials was then filled into hard gelatine capsules or pressed into tablets so that, with a total weight of 320 mg., each capsule or tablet contains 50 mg. of Compound A and 15 mg. of Compound B. The tablets were preferably coated in known manner.

EXAMPLE 2.

Two-layer tablets.

| Compound A | 1000.0 g. |
|---|---|
| lactose (DAB) | 1880.0 g. |
| sodium lauryl sulfate (USP) | 120.0 g. | were mixed together and micronized. The mixture was then mixed with

| lactose (DAB) | 1076.0 g. |
|---|---|
| sodium carboxymethylamylopectin | 200.0 g. |
| highly dispersed silicic acid | 4.0 g. | and granulated with water in known manner, dried and sieved. The granulate was mixed with

| corn starch (DAB) | 100.0 g. |
|---|---|
| magnesium stearate (USP) | 20.0 g. |

This active material-containing mixture was used as the first layer with a weight of 220 mg., containing 50 mg. of Compound A.

| Compound B | 600.0 g. |
|---|---|
| lactose (DAB) | 780.0 g. |
| corn starch (DAB) | 600.0 g. | were mixed together, granulated in known manner with an aqueous paste made from

| corn starch (DAB) | 80.0 g. |
|---|---| dried and sieved. The granulate obtained was mixed with

| cellulose, microcrystalline | 400.0 g. |
|---|---|
| sodium carboxymethylamylopectin | 120.0 g. |
| magnesium stearate | 20.0 g. |

The mixture was used as the second layer with a weight of 130 mg., containing 30 mg. of Compound B.

The production of the two-layer tablets was carried out in tabletting machines suitable for this purpose. The tablets are preferably coated in known manner.

The compounds of this invention possess outstanding diuretic and saluretic properties. In order to establish the effectiveness of compounds representative of this invention as therapeutic agents for diuretic and saluretic purposes, the following series of tests were carried out.

The test animals were female Sprague-Dawley rats each weighing between 170–220 grams. The test animals were kept in climate controlled rooms at 23 ± 1° C. and a relative humidity of 60 ± 5 percent for at least 1 week prior to the tests. On the evening prior to the test day (i.e., 16 hours prior to administration of test compounds), the rats were left without food and had access only to drinking water. During the tests, groups of 5 animals each were placed into metabolic cages and six such groups of animals were used in the tests. The test compounds were administered to the test animals as a suspension in 1% methyl cellulose at the rate of 10 milliliters per kg. of body weight of each rat. The test preparations were administered per os. The dosage in terms of milligrams of test compounds per kg. of body weight is set forth in Table 1 below. Prior to the test and after 6 hours subsequent to the test, the bladders of the rat were emptied by squeezing, the urine content was measured, the chloride content in the urine was determined by titration, and sodium and potassium were determined by flame photometric tests.

The results are set forth in Table 1 below in which the following designations are again used.

5-(4-Chloro-5-sulfamoyl-2-thenyl-aminophenyl)-tetrazole: Compound B 3-(3-Oxo-7α-acetylthio-17β-hydroxy-4-androsten-17α-yl)-propionic acid-γ-lactone (Spironolactone or Aldactone): Compound A

TABLE 1

DIURETIC EFFECTIVENESS IN PER OS ADMINISTRATION IN RATS
(Test compounds in 1% methyl cellulose suspension)

| Test compound | Dosage (mg/kg) | Separation/kg. during 0 – 6 hours | | |
|---|---|---|---|---|
| | | Na$^+$ | K$^+$ | Na/K |
| Control | — | 0.485 ±0.053 | 0.454 ±0.041 | 1.07 ±0.08 |
| Compound B | 25 | 0.448 ±0.07 | 0.406 ±0.04 | 1.08 ±0.15 |
| Compound B | 50 | 2.38 ±0.32 | 1.071 ±0.06 | 2.18 ±0.2 |
| Compound A | 50 | 0.812 ±0.07 | 0.146 ±0.03 | 6.44 ±1.05 |
| Compounds B and A | 25 +50 | 0.994 ±0.052 | 0.207 ±0.023 | 5.0 ±0.37 |
| Compounds B and A | 50 +50 | 1.791 ±0.135 | 0.358 ±0.017 | 4.98 ±0.24 |

Note. - Na$^+$, and K$^+$ values reported as milliequivalents

The data set forth in Table 1 show that the effectiveness of Compound B begins between 25 and 50 mg./kg. specifically in the form of an enhanced desired sodium excretion with a relatively small potassium excretion. This relationship is reflected in a somewhat higher sodium/potassium quotient. Also Compound A leads, in a concentration of 50 mg./kg. to increased sodium excretion and still less potassium excretion than induced by Compound B.

The combination of Compounds A and B results in a balanced electrolyte excretion (enhanced sodium excretion and small potassium excretion relative to Compounds A and B applied separately). Compound A uder these conditions counteracted the excessive potassium excretion induced by higher and longer application of Compound B.

The compounds of this invention are used in diuretic and saluretic applications in a manner known to those skilled in the art. For instance, they may be administered in tablet form, in which a tablet may contain 40 to 400 milligrams of active substance, or in liquid form in, e.g., 2 milliliters ampules. Typical dosage rates are one tablet per day at the higher active substance/tablet contents, or, if no effect is gained, two additional tablets after 6 hours and as needed. Specific use applications and formulations are similar to those for the standard diuretic substance sold under the trademark "Lasix" by Farbwerke Hoechst, AG, Germany.

It will be understood that the specification and examples are illustrative but not limitative of the present invention and that other embodiments within the spirit and scope of the invention will suggest themselves to those skilled in the art.

What is claimed is:

1. Pharmaceutical composition for treating hydropic conditions comprising
   a. 10 to 100 parts by weight of at least one member of 5-(4-chloro-5-sulfamoyl-2-thenylaminophenyl)-tetrazole and the parmacologically compatible salts thereof,
   b. 50 parts by weight of 3-(3-oxo-7α-acethylthio-17β-hydroxy-4-androsten-17α-yl)-propionic acid-γ-lactone, and
   c. a pharmaceutical diluent or carrier.

2. Pharmaceutical composition as claimed in claim 1, comprising 50 parts by weight of 3-(3-oxo-7α-acetylthio-17β-hydroxy-4-androsten-17α-yl)-propionic acid-γ-lactone and 25 to 50 parts by weight of 5-(4-chloro-5-sulfamoyl-2-thenylaminophenyl)-tetrazole.

3. Pharmaceutical composition according to claim 2, comprising 50 parts by weight of 3-(3-oxo-7α-acetylthio-17β-hydroxy-4-androsten-17α-yl)-propionic acid-γ-lactone and 15 to 30 parts by weight of 5-(4-chloro-5-sulfamoyl-2-thenylaminophenyl)-tetrazole.

4. Pharmaceutical composition according to claim 1, wherein the pharmaceutical diluent or carrier is solid and wherein the composition additionally contains at least one coloring material or flavoring material.

5. Pharmaceutical composition according to claim 1, in the form of a tablet or dragee.

6. Pharmaceutical composition according to claim 1, wherein the pharmaceutical diluent or carrier is liquid and sterile and pyrogen-free.

7. Method for treating hydropic conditions which comprises administering to a subject an effective amount of a pharmaceutical composition comprising
   a. 10 to 100 parts by weight of at least one member of 5-(4-chloro-5-sulfamoyl-2-thenylaminophenyl)-tetrazole and the pharmacologically compatible salts thereof,
   b. 50 parts by weight of 3-(3-oxo-7α-acethylthio-17β-hydroxy-4-androsten-17α-yl)-propionic acid-γ-lactone, and
   c. a pharmaceutical diluent or carrier.

8. Method as claimed in claim 7 wherein said pharmaceutical composition comprises 50 parts by weight of 3-(3-oxo-7α-acetylthio-17β-hydroxy-4-androsten-17α-yl)-propionic acid-γ-lactone and 25 to 50 parts by weight of 5-(4-chloro-5-sulfamoyl-2-thenylaminophenyl)-tetrazole.

9. Method as claimed in claim 7 wherein said pharmaceutical composition comprises 50 parts by weight of 3-(3-oxo-7α-acetylthio-17β-hydroxy-4-androsten-17α-yl)-propionic acid-γ-lactone and 15 to 30 parts by weight of 5-(4-chloro-5-sulfamoyl-2-thenylaminophenyl)-tetrazole.

10. Method as claimed in claim 7 wherein said pharmaceutical diluent or carrier is solid and wherein the composition additionally contains a coloring and/or flavoring material.

11. Method as claimed in claim 7 wherein said pharmaceutical composition is in the form of a tablet or dragee.

12. Method as claimed in claim 7 wherein said pharmaceutical diluent or carrier is liquid and sterile and pyrogen-free.

* * * * *